United States Patent [19]
Elford et al.

[11] Patent Number: 5,350,770
[45] Date of Patent: Sep. 27, 1994

[54] THERAPEUTIC PROCESS FOR THE TREATMENT OF SEPTIC SHOCK

[76] Inventors: Howard L. Elford, 3313 Gloucester Rd., Richmond, Va. 23227; Bartholomeus van't Riet, 3419 Noble Ave., Richmond, Va. 23222

[21] Appl. No.: 919,907

[22] Filed: Jul. 28, 1992

[51] Int. Cl.$^5$ ............................. A61K 31/165
[52] U.S. Cl. ..................... 514/575; 514/836; 514/921
[58] Field of Search ............ 514/575, 836, 921

[56] References Cited

U.S. PATENT DOCUMENTS 4,623,659 11/1986 van't Riet et al. ........... 514/508

OTHER PUBLICATIONS

*Ann. Intern. Med.*, 115 464–6 (1991).
Broner et al, *Crit. Care Med.* 16 848 (1988).
Bone Ann. Int. Med. 115 457 (1991).
Jacobs et al Critical Care Clinics 5 9 (1989).
Rackow JAJA 266 548 (1991).
Jeff Johnston The Journal of NIH Res. 3 61 (1991).
McKechnie et al Circ. Shock 19 428 (1986).
Pearce et al Arch. Surg. 120 937 (1985).
Sharpe et al J. Appl. Physiol. 69 1893 (1990).

*Primary Examiner*—Marianne M. Cintins
*Assistant Examiner*—William R. A. Jarvis
*Attorney, Agent, or Firm*—James L. Rowe

[57] ABSTRACT

A therapeutic process for treating septic shock comprising the administration of a polyhydroxy-substituted benzamide or phenylacetamide derivative to a human suffering from, or in danger of contracting, septic shock.

1 Claim, No Drawings

THERAPEUTIC PROCESS FOR THE TREATMENT OF SEPTIC SHOCK

This invention relates to a therapeutic procedure for the treatment and/or prevention of septic shock.

It is an object of this invention to provide drugs capable of modulating the physiological and pathological effects of septicemia (bacteremia) which can frequently lead to septic shock and death. This and other objects will become apparent from the following specification.

BACKGROUND OF THE INVENTION

Septic shock is an often fatal condition that results from severe infections, most often caused by Gram-negative bacteria including *Escherichia coli, Pseudomonas aeruginosa* and *Klebsiella* and *Bacteroides* species. Gram-positive bacterial infections can also lead to septic shock, particularly those caused by *Staphylococcus aureus* and the Pneumococci. The bacterial infections can be acquired via the usual routes-ingestion of contaminated food or water-but can also result as a consequence of surgical procedures including catherization and implantation of prosthetic devices. In addition, patients with depressed immune function-for example, cancer chemotherapy patients-are also susceptible to overwhelming bacterial infections which a patient with a normal immune system could handle easily.

The sequence of events that evolves into septic shock is initiated by the release of large quantities of a bacterial endotoxin into the blood stream in the case of Gram-negative organisms or of the release of a comparable product-cell wall substances-in the case of Gram-positive bacteria, yeast and fungal infections. The bacterial endotoxin is a component of the bacterial cell wall. The active part of the endotoxin is a lipopolysaccharide (LPS). LPS consists of three parts; an oligosaccharide side chain which varies among bacterial species, and two less variable parts, a core polysaccharide and Lipid A. LPS binds to immunoglobin M and this complex activates the complement system with the release of C3b, which material in turn activates the polymorphonuclear leukocytes (PMN), monocytes, neutrophils, macrophage and endothelial cells. The activation of these substances stimulates the release of several mediators of septic shock including tumor necrosis factor (TNFalpha) interleukin-1 (IL-1) and other interleukins including IL6 and IL-8, platelet-activating factor (PAF), prostaglandins and leukotrienes-see *Ann. Intern. Med.* 115 464–6 (1991) for a comprehensivelisting. Of the above, the two cytokines TNFalpha and IL-1 lead to many of the physiologic changes which eventuate into septic shock.

The activated PMNs, among other mediators, cause the formation of oxygen-containing free-radicals. These free-radicals are produced as part of the body's defense against the invasion of foreign organisms and their toxic products. PMN specifically generates the superoxide anion radical (*$O_2$—). This free-radical when acted upon by the enzyme superoxide dismutase (SOD) forms hydrogen peroxide. Excess hydrogen peroxide in the presence of iron generates a second oxygen-containing free-radical, the hydroxyl free-radical (*OH). In addition, activated neutrophils can generate oxyradicals by stimulating the NADPH oxireductase reaction. The release by neutrophils of both oxyfree-radicals and proteases causes extensive damage to endothelial cells. In addition, adhesion of activated neutrophils to endothelial cells leads to vascular permeability, which in turn causes much of the damage associated with septicemia and septic shock.

The LPS-stimulated macrophages also release other free-radicals, including oxyfree-radicals from arachidonic acid metabolism, which free-radicals can also cause extensive damage to endothelial cells. These damages lead to coagulation deficiencies and circulatory collapse which in turn lead to hypotension, tissue damage, multi-organ failure and death. Thus, excess production of the above mentioned free-radicals is linked to the mortality associated with septic shock.

Current treatment for septicemia includes administration of antibiotic to kill the invading bacteria and infusion of fluids to counter hypotension. Unfortunately, the bacteria killed by the antibiotic can worsen the septicemia by releasing additional quantities of endotoxin and LPS. Other possible therapeutic procedures include use of monoclonal antibodies to bind LPS and products to block the action of cytokines by again using monoclonal antibodies to bind TNFalpha and IL-1.

Another possible treatment method for septicemia would be the use of drugs that would either stop the production of oxyfree-radicals or would act to neutralize such radicals, as by a scavenging action or a free-radical chain reaction terminating action. Of particular importance would be the provision of drugs that that can scavenge the superoxide anion radical and the hydroxyl free-radical. It is thus a further object of this invention to provide free-radical scavengers and compounds capable of terminating free-radical chain reactions in vivo. Since such free-radicals contribute materially to the deleterious physiologic changes which culminate in septic shock, such drugs should help to alleviate the consequence of septicemia and hence avoid the end result of those effects,

SUMMARY OF THE INVENTION

This invention provides a therapeutic process for the prevention or treatment of septic shock which comprises administering to a human suffering from septicemia or septic shock and in need of treatment, an amount of a polyhydroxy-substituted benzamide or phenylacetamide derivative of the following formula sufficient to modulate the pathological consequences of septicemia and of septic shock produced by said septicemia and thus prevent death or serious disease caused by said septicemia

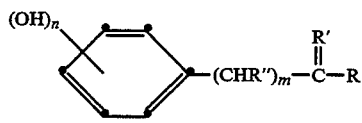

Formula I wherein n is 2–5, m is 1 or 0, R is $NH_2$, NHOH, O—$C_{1-3}$ alkyl or O-phenyl, R' is O, NH or NOH, when R and R' are taken together to form ↑N, and R" is H or OH. Also included within the scope of the above formula are the pharmaceutically-acceptable salts of compounds depicted thereby where chemically feasible, as well as the phenolic acetyl or similar phenolic esters of compounds according to the above formula which, by their ready hydrolysis to the free hydroxyl derivative, act as pro-drugs.

Illustrative of the polyhydroxy-substituted phenyl ring in the above formula are included 2,3-dihydroxyphenyl, 3,4-dihydroxyphenyl, 2,5-dihydroxyphenyl, 2,6-dihydroxyphenyl, 2,3,4-trihydroxyphenyl, 2,4,5-trihydroxyphenyl, 3,4,5-trihydroxyphenyl, 2,4,5-trihydroxyphenyl, pentahydroxyphenyl, 2,3,4,5-tetrahydroxyphenyl and the like groups.

In the above formula, when m is 1 and R" is H, a phenylacetic acid derivative is denominated. When m is 1 and R" is OH, a mandelic acid derivative is represented. When m is 0, R is NHOH and R' is O, an N-hydroxybenzamide (formerly named as a benzohydroxamic acid) is represented; when R is $NH_2$ and R' is NH, a benzimidamide (formerly a benzamidine) is represented; when R is NHOH, and R' is NH, an hydroxy benzimidamide (formerly a benzamidoxime) is shown; when R is NHOH and R' is NOH, an N,N'-dihydroxy benzimidamide (formerly an hydroxyamidoxime) is represented; and when R is O-phenyl and R' is NH, the resulting compounds are named as benzimidates (rather than benzamidates as previously). In the above formula, when R is $O—C_{1-3}$ alkyl, the alkyl groups represented include methyl, ethyl, n-propyl and isopropyl.

Compounds represented by Formula I above are fully illustrated in U.S. Pat. Nos. 4,253,322, 4,623,659, 2,848,430 and 3,629,443. Methods for the preparation of those compounds are also fully disclosed in those patents, as well as in the many references cited therein. In particular, the compounds listed in Cols. 2 and 3 of U.S. Pat. No. 4,623,659 illustrate the scope of the compounds represented by Formula I (always remembering that the approved nomenclature for these structures has changed since 1983 when the application that resulted in that patent was filed) and the disclosure of U.S. Pat. No. 4,623,659 is incorporated herein, and made a part hereof, by reference.

It will be apparent to those skilled in the art that other phenolic blocking groups, in addition to the acetyl group specified above, may be employed to provide pro-drugs, including other lower alkanoic esters, phenacyl esters and the like, the only requirement being that the mammalian organism is easily able to convert the pro-drug to the active drug.

As stated above, the therapeutic processes of this invention are useful in combating septicemia and septic shock in mammals. As evidence of such activity, mice were pretreated with LPS to induce a septicemic state which rapidly progressed to septic shock and death. Thus, this treated mouse served as a model for the same diseases and disease states in man. The chief drug employed in such testing was DIDOX (N,3,4-trihydroxybenzamide, a compound coming within the scope of Formula I above. A second compound, VF 233 (N,3,4,5-tetrahydroxybenzimidamide hydrochloride) was also used in one test.

BIOLOGICAL TESTING

The following protocol was used to determine the ability of compounds according to Formula I above to alleviate the deleterious biological consequences of septicemia and septic shock: Groups of 5–10 female CD-1 (CD2F1) mice weighing between 18–25 g. were used as the test mammal. All mice were warmed prior to treatment via a heating pad in order to dilate their veins. The vasodilated mice were then injected with endotoxin lipopolysaccharide (E. coli lipopolysaccharide 0111:B4, TCA extract, obtained from SIGMA Chem Co.) by IV (intravenous) injection into a tail vein. The usual dose of endotoxin lipopolysaccharide (LPS) was 0.04 mcg/g., micrograms per gram of mouse body weight. This injection was immediately followed by an IV injection of actinomycin D (A) at a dosage of 0.8 mcg/g. of mouse body weight. Actinomycin is known to enhance the sensitivity of mice to LPS. During the various injections, the mice were restrained in order to minimize trauma.

The above procedure was designed to elicit the symptoms and consequences of septicemia and septic shock and to mimic the conditions and effects of septic shock and septicemia in humans.

In each experiment, one group or more of mice were retained as control groups and injected IP (intraperitoneally) with a volume of saline equivalent to the volume of the drug plus carrier injected into the treated mice. The compound or compounds under test were administered IP in single or multiple doses before or after the administration of the LPS-A. All mice were observed on an hourly basis for 12 hrs. and then observed at 24 and 48 hrs. The observations included visual assessment of the animal's appearance, activity and movement and whether or not they were eating and/or drinking. The primary indicator of the efficacy of each treatment method was, however, the life span of the mice. Under the above protocol, untreated mice suffered 100% mortality and any increase in life span indicated that the particular treatment method had some efficacy in combatting the deleterious effects of the LPS-A injection.

EXPERIMENT 1

In this experiment, a control group of 5 mice received 0.5 ml of saline IP 2 hrs. prior to the LPS-A injection. With the treated groups, one group of 5 mice (DIDOX A) were injected with DIDOX, 250 mg/kg (milligrams per kilogram of mouse body weight) IP 2 hrs. prior to, and 30 min. after, LPS-A injection. A second treated group (DIDOX B) received 450 mg/kg of DIDOX IP 15 min. after LPS-A treatment. A third group of mice received 125 mg/kg IP of VF 233(N,3,4,5-tetrahydroxybenzimidamide.HCl) 2 hr prior and 15 min. after LPS-A treatment. A fourth group of mice received 20 units of SOD (superoxide dismutase) per gram of body weight 2 hrs. prior to LPS-A treatment. The five groups of mice were evaluated at various hourly intervals up to 96 hrs. The average life span for the above groups were as follows: Control group 7.6 hrs., VF 233 7.2 hrs., SOD group 6.8 hrs., DIDOX A 58.1 hrs. (8-fold longer than the control group), DIDOX B 44.4 hrs. with one survivor (6-fold longer than the control group).

EXPERIMENT 2

In this experiment, 6 groups of 10 mice each were used. 3 groups were control groups, receiving only saline injection at times and volumes corresponding to the treatment group injection times and volumes. The treatment groups consisted of (A) 250 mg/kg DIDOX 2 hrs. prior and 30 min. after LPS-A injection; (B) 450 mg/kg DIDOX 15–30 min. after LPS-A injection; (C) 20 units SOD administered 2 hrs. prior and 15–30 min. after LPS-A treatment. The results of this experiment were as follows: (A) Control group-5 survived for 12 hrs. but all were dead by 24 hrs. DIDOX treatment group-one dead at 5 hrs., 4 dead at 12 hrs., one more dead by 24 hrs. and 5 (50%) survivors. (B) Control group-all dead by 6 hrs. Didox treatment group-one dead at 9 hrs., 5 more by 12 hrs., 3 at 24 hrs., one survivor. (C) Control group-9 dead at 6 hrs. and the last mouse by 24 hrs., SOD treatment group-6 dead by 12 hrs., the remaining 4 by 24 hrs.

EXPERIMENT 3

Similar to Experiment 1 with a DIDOX A and a DIDOX B treatment group and a control group for each. The results were as follows: Control groups-all dead by 9 hrs., DIDOX A group-no deaths till 8 hrs., 6 survived 12 hrs., 2 alive at 24 hrs. and one indefinite survivor; DIDOX B group-4 alive at 12 hrs., 2 at 24 hrs. and 2 indefinite survivors.

EXPERIMENT 4

Five mice per group. Control group were injected with saline IP 15 min. after LPS-A treatment. One DIDOX group was injected with 450 mg/kg of drug 15 min. after LPS-A injection. A second DIDOX group was given a 450 mg/kg injection 2 hrs. after LPS-A treatment and a third DIDOX group was injected with the drug at the same dosage 15 min. prior and 1 hr. post LPS-A treatment, A fourth Didox group received the drug at a 300 mg/kg dose rate 15 min. and 8 hrs. after LPS-A injection and a fifth Didox group followed the same injection schedule but with a 450 mg/kg dosage. The results of this experiment were as follows: Control group-4 out of 5 dead at 5 hrs. and the sixth at 6 hrs. First Didox group-one dead at each of 9, 12 and 24 hrs. with 2 long-term survivors. Second DIDOX group-2 dead at 6 hrs., one more by 9 hrs. and two more by 24 hrs. Third DIDOX group-all mice survived 12 hrs., 4 died by 24 hrs. and there was one survivor. Fourth DIDOX group-only one dead by 12 hrs., 3 more by 24 hrs. and one survivor. Fifth DIDOX group-one dead at 6 hrs., remaining 4 were long-term survivors.

EXPERIMENT 5

10 mice per group. Control group was injected IP with saline 15 min. after LPS-A treatment. All DIDOX groups received 450 mg/kg DIDOX IP 15 min. after LPS-A treatment. DIDOX A group-no additional treatment. DIDOX B group-an additional 450 mg/kg injection 2 hrs. after LPS-A injection. DIDOX C group-same dose but second injection at 6 hrs. after LPS-A treatment. Control group for second half of experiment treated the same as first control group. DIDOX A' group-same as DIDOX A; DIDOX D group-same as DIDOX B group but second injection at 4 hrs. Results: E-same as DIDOX C but second injection at 8 hrs. Results: Control group-only 3 survivors at 6 hrs. and all animals are dead by 9 hrs. DIDOX A group-all are survivors at 9 hrs., and there are 8 survivors at 12 hrs. and there are 4 long-term survivors. DIDOX B group-7 mice are survivors at 9 and 12 hrs. and 5 are long-term survivors. DIDOX C group-all mice are survivors at 9 hrs., 6 mice are survivors at 24 hrs. and beyond. Second half of experiment-second control group-all dead by hour 6. DIDOX A' group-only 3 survivors at 12 hrs. but 2 long-term survivors. DIDOX D group-only 2 dead at 12 hrs. but no long-term survivors. This last group also was superior to other groups in exterior appearance, movement, appetite and water consumption prior to death. DIDOX E group-one dead at 5 hrs., no more deaths at 6 hrs., 5 more dead at 8 hrs., 3 additional dead at 9 hrs. and all dead by 12 hrs. The following table summarizes deaths in treated and control groups of mice in Experiments 2-5.

PROTECTION AGAINST ENDOTOXIN TOXICITY BY DIDOX

| Treatment Group | 1 hr. | 5 hr. | 6 hr. | 9 hr. | 12 hr. | 24 hr. |
|---|---|---|---|---|---|---|
| EXPERIMENT 2 | | | | | | |
| DIDOX A | 10 | 9 | 9 | 8 | 7 | 6(5)* |
| Control | 10 | 9 | 8 | 7 | 5 | 0 |
| DIDOX B | 10 | 10 | 10 | 9 | 4 | 1(1) |
| Control | 10 | 9 | 0 | | | |
| SOD | 10 | 8 | 7 | 5 | 4 | 0 |
| Control | 10 | 8 | 1 | 1 | 1 | 0 |
| EXPERIMENT 3 | | | | | | |
| CONTROL | 10 | 9 | 2 | 0 | | |
| DIDOX A | 10 | 10 | 10 | 7 | 6 | 2(1) |
| DIDOX B | 10 | 10 | 10 | 8 | 6 | 2(2) |
| EXPERIMENT 4 | | | | | | |
| DIDOX 1 | 5 | 5 | 5 | 4 | 3 | 2(2) |
| DIDOX 2 | 5 | 5 | 3 | 2 | 2 | 0 |
| DIDOX 3 | 5 | 5 | 5 | 5 | 5 | 1(1) |
| DIDOX 4 | 5 | 5 | 5 | 4 | 4 | 1(1) |
| DIDOX 5 | 5 | 5 | 4 | 4 | 4 | 4(4) |
| Contol | 5 | 1 | 0 | | | |
| EXPERIMENT 5 | | | | | | |
| Control | 10 | 8 | 3 | 0 | | |
| DIDOX A | 10 | 10 | 10 | 10 | 8 | 4(4) |
| DIDOX B | 10 | 10 | 10 | 7 | 7 | 5(5) |
| DIDOX C | 10 | 10 | 10 | 10 | 9 | 6(6) |
| Control | 10 | 3 | 0 | | | |
| DIDOX A' | 10 | 10 | 10 | 4 | 3 | 2(2) |
| DIDOX D | 10 | 10 | 10 | 9 | 8 | 1 |
| DIDOX E | 10 | 9 | 9 | 1 | 0 | |

*figure in parenthese gives number of long-term survivors

It is readily apparent that treatment of mice challenged with LPS in an effort to duplicate the physiological conditions accompanying septicemia or septic shock (see, for example, Broner et al, *Crit. Care Med.* 16 848 [1988]), with a compound coming within the scope of Formula I above, prolongs the life of such challenged mice, regardless of dose, timing of dose, or dosing prior to, or after, challenge. Obviously, certain dosage regimens are superior to others in terms of mouse survival rate. Furthermore, the finding of indefinite survivors in the treated group is most unusual and again indicates the efficacy of the therapeutic processes disclosed and claimed in this specification. Finally, it should be noted that the above data are contrary to the findings of Broner et al (loc. cit.) who found SOD effectively prolonged the life of endotoxinchallenged mice, whereas a free-radical scavenger (free-radical chain terminator), N-acetyl cysteine, did not prolong the lifespan of endotoxin-challenged mice.

Although DIDOX was adminstered in saline IP, other parenteral routes (IV, IM, intradermal or intrathecal) may also be used. Drugs useful in the therapeutic procedures of this invention can readily be formulated for such parenteral administration in accordance with the skill of the art. The same considerations apply to oral medications containing DIDOX or other drug according to Formula I; ie., tablets, filled gelatin capsules, gelseals, liquid formulations and the like. As will be apparent to those skilled in the art, effective dose levels will vary according to the mode of administration. For example, oral dose levels would be higher than IV dose levels.

We claim:

1. A therapeutic process for the treatment of septicemia or septic shock comprising administering to a human suffering from septicemia or septic shock and in need of treatment an amount of N,3,4-trihydroxybenzamide or pharmaceutically acceptable salts thereof, wherein the amount is sufficient to modulate the pathological consequences caused by septicemia or septic shock.

* * * * *